US008450339B2

(12) United States Patent
Moesgaard et al.

(10) Patent No.: US 8,450,339 B2
(45) Date of Patent: *May 28, 2013

(54) COMPOSITIONS FOR TREATMENT OF COMMON COLD

(75) Inventors: Hanne Anette Moesgaard, Præstø (DK); Karin Lowenstein Christensen, Frederiksberg (DK)

(73) Assignee: Takeda Pharma A/S, Roskilde (DK)

( * ) Notice: Subject to any disclaimer, the term of this patent is extended or adjusted under 35 U.S.C. 154(b) by 504 days.

This patent is subject to a terminal disclaimer.

(21) Appl. No.: 12/654,145

(22) Filed: Dec. 11, 2009

(65) Prior Publication Data

US 2010/0093783 A1 Apr. 15, 2010

Related U.S. Application Data

(63) Continuation of application No. 10/489,655, filed as application No. PCT/IB02/03828 on Sep. 18, 2002, now Pat. No. 7,652,030.

(30) Foreign Application Priority Data

Sep. 18, 2001 (DK) .................................. 2001 01356

(51) Int. Cl.
*A61K 31/4745* (2006.01)
*A61K 31/137* (2006.01)
*A61K 31/135* (2006.01)

(52) U.S. Cl.
USPC ............ 514/291; 514/304; 514/401; 514/649

(58) Field of Classification Search
USPC .................................. 514/291, 304, 401, 649
See application file for complete search history.

(56) References Cited

U.S. PATENT DOCUMENTS

| | | | |
|---|---|---|---|
| 5,376,365 A | 12/1994 | Dikstein | |
| 5,955,058 A | 9/1999 | Jager et al. | |
| 6,045,778 A | 4/2000 | Jager et al. | |
| 7,652,030 B2 * | 1/2010 | Moesgaard et al. | 514/291 |
| 2001/0008632 A1 | 7/2001 | Freund et al. | |
| 2004/0191177 A1 | 9/2004 | Maerz | |

FOREIGN PATENT DOCUMENTS

| | | |
|---|---|---|
| CA | 2376121 | 12/2001 |
| EP | 0 780 127 | 6/1997 |
| JP | 8-509459 | 10/1996 |
| WO | 93 09764 | 5/1993 |
| WO | 94/05330 | 3/1994 |
| WO | 94/13262 | 6/1994 |
| WO | 98 48839 | 11/1998 |
| WO | 99/38492 | 8/1999 |
| WO | 99/65464 | 12/1999 |
| WO | 00/78297 | 12/2000 |

OTHER PUBLICATIONS

International Search Report mailed May 27, 2003 in International (PCT) Application No. PCT/IB02/03828.

P. Borum, "Nasal Disorders and Anticholinergic Therapy", Postgraduate Medical Journal, McMillan Press, Basingstoke, GB, vol. 63, No. SUPPL. 1, pp. 61-68, 1987, XP001036578, ISSN: 0032-5473.

P. Borum et al., "Ipratopium Nasal Spray: A New Treatment for Rhinorrhea in the Common Cold", American Review of Respiratory Disease, New York, NY, US, vol. 123, No. 4, pp. 418-420, 1981, XP001039527, ISSN: 0003-0805.

Bundesverband Der Pharmazeutischen Industrie E V: "Rote Liste 1995", Rote Liste 1995. Arzneimittelverzeichnis Des BPI UND VFA, Aulendorf/Wurtt., Editio Cantor, De, vol. Ed. 1995, p. 71041, XP002241063, p. 71041, "Otriven".

Editions Du Vidal: "Dictionnaire Vidal 1996", Dictionnaire Vidal 1996, Patis, Editions Du Vidal, FR, p. 139, XP002241064 ISBN: 2-85091-078-3, p. 139, "Atrovent".

Abstract of P. Borum et al., "Nasal reactivity in rhinitis", European Journal of Respiratory Diseases, 64, Suppl. 128, pp. 65-71, 1983.

I. Grabowska et al., "Badanie hydrolitycznego rozkladu chlorowodorku ksylometazoliny", Acta Polon Pharm XLI, Nr. 3, pp. 359-363, 1984.

Abstract of G. Bell et al., "Hydrolysis kinetics of ipratropium bromide in aqueous solution", Pharm. Res: 7: Suppl. S129, 1990.

Abstract of A. Pitkaranta et al., "Combined intranasal ipratropium bromide and oxymetazolin in experimental rhinovirus infection", Am J. Rhinol. Mar.-Apr. 1998; 12(2):125-9.

Boehringer Ingelheim AB, "Läkemedelsmonografi of Atrovent Nasal", Information from the Swedish Medical Products Agency, 1998; 9(8): 232-34, latest amendments Aug. 15, 2002.

Dr. Josef Scholtholt et al. "Rote Liste 1996." Frankfurt, Nov. 1995. (With English language translation.).

Notice of Reasons for Rejection mailed Aug. 25, 2008 in counterpart Japanese Application No. 2003-528530 with English translation.

International Preliminary Examination Report completed Dec. 15, 2003 in International (PCT) Application No. PCT/IB02/03828.

* cited by examiner

*Primary Examiner* — Jennifer M Kim
(74) *Attorney, Agent, or Firm* — Wenderoth, Lind & Ponack, L.L.P.

(57) ABSTRACT

New stable compositions comprising the combination of a topically active vasoconstrictor and a topically active anticholinergic drug are disclosed. Preferably, the composition comprises ipratropium or a salt thereof in combination with xylometazoline hydrochloride and a salt thereof. Upon topically administering such compositions to a nasal mucosa in individuals suffering from the common cold the symptoms of rhinorrhea are significantly reduced.

23 Claims, No Drawings

COMPOSITIONS FOR TREATMENT OF COMMON COLD

This application is a continuation application of Ser. No. 10/489,655, filed May 12, 2004 now U.S. Pat. No. 7,652,030, now allowed, which is a 371 application of International Application No. PCT/IB02/03828, filed Sep. 18, 2002.

FIELD OF INVENTION

The invention relates to the combination of two groups of therapeutically active agents, one group with local stimulating effect on alpha-adrenergic receptors in the nasal epithelium and another group with local anticholinergic effect on the nasal epithelium. Interesting agents are xylometazoline or salts thereof and ipratropium or salts thereof. Furthermore, the invention relates to the treatment of common cold using these agents.

BACKGROUND OF THE INVENTION

Drugs for the symptomatic relief of common cold symptoms have been widely used for decades. Common cold is a self-limited illness, typically of short duration with usually mild symptoms normally lasting for a few days up to about two weeks in severe cases. The symptoms of a common cold include sneezing, rhinorrhea (runny nose), nasal congestion, sore or scratchy throat, cough, hoarseness, and mild general symptoms like headache, chilliness, and general malaise.

More than 200 different viruses are known to cause the symptoms of the common cold. Among these, the rhinoviruses account for more than 30% of colds in adults. Other common cold inducing viruses include the Corona viruses, the Influenza viruses, A, B and C. Infections by viruses may be associated with otitis media, sinusitis, exacerbation of asthma and chronic lung disease, and, in infants, serious lower respiratory tract disease.

Currently, however, no antiviral drug is available for the treatment of common cold. Therefore, treatment is based on the managing of symptoms associated with the common cold.

A number of medicaments have been developed for the treatment of symptoms associated with common cold through stimulation of the adrenergic receptors in the sympathetic nervous system of the nose or through competitive inhibition of cholinergic receptors.

Topical sympathomimetic decongestants such as imidazoline alpha-adrenergic agonist (a vasoconstrictor), e.g. xylometazoline, have been administered as either nasal spray or nose-drops in order to relieve nasal congestion and prevent sinusitis. A widely used medicament on the market comprising xylometazoline is the nasal spray, Zymelin®. Other topical nasal decongestants include Phenylephrine, Oxymetazoline, Naphazoline, Tetrahydrozyline, Ephedrine, Etaphedrine, Clonazoline, Dimepropion, Fenoxazoline and Indanazoline.

Agents with local anticholinergic activity in the upper respiratory tract, such as ipratropium, a derivative of N-isopropyl noratropine, are also useful for treating symptoms of common cold. Ipratropium bromide is today used as an agent efficacious in normalising nasal secretion in patients with rhinorrhea associated with perennial rhinitis and in reducing nasal secretion in patients suffering from common cold. Ipratropium bromide is available on the market as a nasal spray, Atrovent®, for the symptomatic treatment of rhinorrhea associated with perennial rhinitis. Other topical nasal anticholinergic agents include oxitropium bromide, anisotropine methylbromide, clidinium bromide, glycopyrrolate and mepenzolate bromide.

Following intranasal administration of xylometazoline hydrochloride, the vasoconstrictor effect generally occurs within five to ten minutes and the effect may last for 5-6 hours and up to 12 hours. Likewise, the maximal effect following administration of ipratropium bromide is reached after 0.5 to 1.5 hrs with a mean duration of 6 hours.

Ipratropium bromide is further reported to irritate the nasal mucosa by desiccating the nasal mucosa, thereby causing discomfort to the user of medicaments comprising ipratropium bromide.

The combination of xylometazoline and ipratropium or suitable derivatives or salts thereof into one medicament for nasal administration will involve that more than one symptom can be treated simultaneously, thereby further reducing the degree to which the patient is affected by the common cold. Furthermore, the number of doses and/or the daily dose needed for achieving the relieving effect on common cold may be reduced.

However, no such medicament exists today. Both agents, ipratropium or salts thereof and xylometazoline or salts thereof, have each been reported in the literature to have poor stability in aqueous solutions. Literature data show that aqueous solutions of xylometazoline hydrochloride and ipratropium bromide have stability optima at pH 2 and pH 3.5, respectively (Grabowska I et al. Acta, Polon Pharm XLI, 359-363, 1984 and Bell G et al. Pharm Res 7: Suppl S129, 1990). Xylometazoline hydrochloride is fairly stable in acidic media, whereas in neutral and alkaline media, the rate of degradation is considerably increased. Ipratropium bromide is an ester and undergoes hydrolysis in aqueous solution to give tropic acid and an alcohol. The hydrolysis increases with increasing/decreasing pH values above pH 3.5 and below pH 3.5. With the aim of providing a medicament comprising the two active agents, the pH should be advantageous for nasal application. Therefore, a medicament for nasal application should not have a pH in the order of the stability optima reported for ipratropium bromide and xylometazoline hydrochloride, respectively, but rather a pH about pH 6 to pH 7. Unfortunately, in this pH range the two agents are subject to degradation.

Formulations comprising ipratropium bromide already exist, e.g. formulated as an aerosol, either containing up to 5% of ipratropium bromide (by weight) or in non aqueous suspensions (U.S. Pat. No. 5,955,058 and WO 99/65464).

Furthermore, the combination of drugs with different pharmacological activity in the treatment or prevention of nasal diseases have been disclosed in the form of a nasal spray (WO94/05330). Preferably, such drugs are anti-inflammatory agents, antihistaminic agents, anticholinergic agents, antiallergic agents or vasoconstrictors. Furthermore, WO98/48839 discloses topically applicable nasal compositions comprising a topical anti-inflammatory agent combined with at least one agent suitable for topical nasal administration and selected from the group consisting of a vasoconstrictor, a neuraminidase inhibitor, a leukotriene inhibitor, an antihistamine, an anti-allergic agent, an anticholinergic agent, an anaesthetic and a mucolytic agent. The compositions may be administered as nasal sprays or as nose drops for the treatment of nasal and sinus conditions. In WO 93/09764, the combination of anti-viral and anti-inflammatory agents is disclosed for the treatment of common cold and related disorders. In one embodiment thereof, the combination include ipratropium and xylometazoline dissolved or suspended in a liquid propellant.

Co-administration of ipratropium and xylometazoline has been investigated by Borum et al. In a trial by Borum et al, each nostril was primed with xylometazoline five minutes prior to ipratropium administration in order to secure adequate distribution of ipratropium to the nasal epithelium (Borum P et al, Am Rev Res Dis, 123, 418-420, (1981) and Borum P et al, European Journal of Respiratory Diseases, 64, Suppl 1281, 65-71, (1983).

SUMMARY OF THE INVENTION

The present inventors have found that a novel composition for simultaneously, coinstantaneously, administration to the nasal cavity of an effective dose of an anticholinergic agent, in particularly ipratropium or a suitable salt thereof, and an α-adrenergic agent, in particularly xylometazoline or a suitable salt thereof, is more effective in reducing the runny nose in individuals suffering from common cold than compositions comprising xylometazoline hydrochloride as the only active agent.

Surprisingly, it was further found that such combinations of two therapeutically active agents, ipratropium and xylometazoline or salts thereof, can be formulated in a composition applicable for nasal administration such that the composition is sufficiently stable in order to allow for storage at 25° C. for at least 9 months. Furthermore, such a formulated composition does not lead to irritation of the nasal mucosa.

Accordingly, in a first aspect, the invention relates to stabilised compositions and/or stabilised dosage units comprising a) ipratropium or a salt thereof and b) xylometazoline or a salt thereof in aqueous solution. Importantly, such compositions may have a pH in the range of about 4 to 7 and/or comprising one or more complex binder(s) and/or one or more antioxidant(s). Preferably, the compositions does not comprise more than two therapeutically active agents.

The combination of local active α-adrenergic stimulating agents and anti-cholinergic agents in the respiratory tract, in particularly ipratropium bromide and xylometazoline, may be directed to the lessening, relief or cure of symptoms associated with common cold despite the cause of the common cold. Accordingly, a second aspect of the invention relates to the use of a combination of topically active α-adrenergic stimulating agents and topically active anti-cholinergic agents, in particularly ipratropium or a salt thereof and xylometazoline or a salt thereof for the preparation of a medicament, wherein the medicament is formulated for mucosal delivery of an effective amount of ipratropium or a salt thereof and xylometazoline or a salt thereof for the treatment of symptoms associated with the common cold and with rhinitis.

Moreover, the invention relates to a method for treatment of symptoms associated with the common cold and with rhinitis by administering a therapeutically effective amount of ipratropium or a salt thereof and xylometazoline or a salt thereof in aqueous solution. Importantly, the administration of the two agents may be conducted simultaneously. That is to say co-instantaneously.

Finally, the invention relates to a method of stabilising ipratropium or a salt thereof and xylometazoline or a salt thereof in aqueous solution comprising the use of at least one agent selected from the group consisting of pH-adjusting agents, anti-oxidants, radical scavengers and complex binders.

DETAILED DESCRIPTION OF THE INVENTION

The term "ipratropium or a salt thereof" is intended to relate to ipratropium, a pharmaceutically acceptable salt thereof, a mixture of ipratropium and one or more pharmaceutically acceptable salts thereof, or a mixture of pharmaceutically acceptable salts of ipratropium.

Likewise, the term "xylometazoline or a salt thereof" is intended to relate to xylometazoline, a pharmaceutically acceptable salt thereof, a mixture of xylometazoline and one or more salts thereof, or a mixture pharmaceutically acceptable salts of xylometazoline.

The term "equivalent to an amount of about . . . of ipratropium bromide" is intended to relate to a specified volume, concentration, or amount of ipratropium bromide provided by a volume, concentration, or amount of ipratropium or a salt thereof, such that the molar or weighed content of said ipratropium or a salt thereof is equivalent to that of said ipratropium bromide. In a most preferred embodiment, the composition, dosage unit, method or use of the present invention comprises the use of ipratropium bromide.

The term "equivalent to an amount of about . . . of xylometazoline hydrochloride" is intended to relate to a specified volume, concentration, or amount of xylometazoline hydrochloride provided by a volume, concentration, or amount of a salt of xylometazoline or a salt thereof, such that the molar or weighed content of said xylometazoline or salt thereof is equivalent to xylometazoline hydrochloride. In a most preferred embodiment, the composition, dosage unit, method or use of the present invention comprises xylometazoline hydrochloride.

The term "formulated" is intended to relate to the selection of excipients, carriers, vehicles, solvents, co-solvents, preservatives, colouring agents, flavouring agents and so forth in the preparation of a medicament using said composition. The term "formulated" is furthermore intended to relate to the selection of the device for delivery of the composition or selection of containment device for administration or storing of the composition.

The term "dosage" relates to the quantity of active drugs administered to a mucosa by means of one delivery operation. In the embodiment, wherein the active drugs are formulated for administration to a nasal mucosa, the term "dosage" relates to the quantity of active drugs administered to one nostril by means of one delivery operation.

The term "delivery operation" is an operation, which delivers a dosage to a mucosa. In the embodiment, wherein the delivery operation is for delivering a dosage to the nasal mucosa, the term "delivery operation" is an operation, which delivers a dosage to one nostril. Preferably, the delivery operation is performed to both nostrils. In one embodiment, a delivery operation is the administration to the nasal cavity of a dosage by means of a delivery system, such as a nasal spray or other means known to the person skilled in the art. Suitable devices are commercially available.

The term "dosage unit" relates to a composition administered by means of one or more delivery operation. In the embodiment, wherein the composition is a liquid, a dosage unit is the volume of the composition administered by means of one or more delivery operation.

The term "daily dose" relates to the quantity of active substances administered to a mucosa during 24 hours by means of one or more delivery operations. In the embodiment, wherein, the active substances are to be administered to the nasal cavity, the daily dose relates to the quantity of active substances administered to both nostrils during 24 hours.

The term "pharmaceutically acceptable salts" is denoted to mean substances that are essentially non-toxic following administration to a mucosa and meet a specified chemical or microbial quality. Pharmaceutically acceptable salts should in general meet the specifications to drug substances as presented in guidelines such as the USP (United States Pharmacopoeia) and the European Pharmacopoeia.

The term "humectant" relates to an agent that brings about a moisturising effect to the target where it is applied.

The term "shelf-life" is intended to mean the period of time, wherein the therapeutically active substances in a composition is stable at ambient conditions, e.g. 25° C. and 60% RH (relative humidity), such that at least 90%, preferably 95%, more preferably 97.5% of the initial amount of said substances is still present in the composition within the specified shelf-life.

The term "stabilised composition" is intended to mean a composition, wherein the content of the therapeutically active substances, such as ipratropium bromide and xylometazoline hydrochloride, is stable such that at least 90% w/w, more preferably 95% w/w, even more preferably 98% w/w of the specified components are present in said composition after at least 9 months of storage at 25° C. and 60% RH in darkness.

The term "mucosal delivery" relates to delivery of a composition to a mucous membrane, such as the buccal or labial mucosa or the mucosa of the respiratory tract, such as the nasal mucosa.

As stated, a first aspect of the invention relates to a stable composition comprising a) ipratropium or a salt thereof and b) xylometazoline or a salt thereof in aqueous solution. A further aspect related hereto, is a stable dosage unit comprising as active compounds a) ipratropium or a salt thereof and b) xylometazoline or a salt thereof in aqueous solution.

A characteristic feature according to the invention is that a composition as well as a dosage unit comprising ipratropium salt or salt thereof and the xylometazoline or a salt thereof in aqueous solution is stable such that at least 80% w/w of the ipratropium or a salt thereof is present in said composition or dosage unit after at least 6 months of storage at 40° C. and 25% RH in darkness. Preferably at least 85% w/w, more preferably 90% w/w, even more preferably at least 95% w/w, most preferably at least 98% w/w of the ipratropium or a salt thereof is present in said composition or dosage unit after at least 6 months of storage at the above-mentioned conditions. Such compositions or dosage units may also be stable such that at least 80% w/w of the xylometazoline or a salt thereof is present in said composition or dosage unit after at least 6 months of storage at 40° C. and 25% RH in darkness. Preferably at least 85% w/w, more preferably 90% w/w, even more preferably at least 95% w/w, most preferably at least 98% w/w of the xylometazoline or a salt thereof is present in said composition or dosage unit after at least 6 months of storage at said conditions.

Moreover, a characteristic feature of the invention includes that a composition as well as a dosage unit comprises low amounts of the breakdown products of the active compounds.

Thus, an aqueous solution comprising ipratropium bromide and xylometazoline hydrochloride is stable such that at most 5% w/w of tropic acid is formed from ipratropium or a salt thereof after storage for at least 4 months at 40° C. and 25% RH in darkness. Preferably at most 4% w/w, at most 3% w/w, more preferably at most 2.5 w/w, such as at most 2%, 1.5% or 1% w/w, even more preferably at most 0.5% w/w such as at most 0.4% w/w and at most 0.3% w/w and even more preferably at most 0.2 w/w and 0.1% w/w of tropic acid is formed from ipratropium or a salt thereof after storage for at least 4 months at 40° C. and 25% RH in darkness.

Suitably, especially for pharmaceutical use, a composition as well as a dosage unit comprising ipratropium or a salt thereof and xylometazoline or a salt thereof is stable for long term storage, such as at least 6 months at ambient conditions, e.g. at 25° C. and 60% RH, protected from day light. However, preferable embodiments of the invention are stable after at least 1 year, more preferably after at least 2 years and even more preferably after at least 3 years of storage at physical conditions of 25° C., 60% RH and protected from day light. Moreover, typical embodiments also include those that are stable at lower or higher temperatures as well as at higher or lower relative humidity. For instance, embodiments may be stable after at least 6 months such as at least after 1 year of storage at 40° C. and 25% RH in darkness. Likewise, typical embodiments of the invention are also stable after at least 6 months such as after at least 1 year of exposure to diffused daylight. Therefore, typical embodiments are stable after at least 6 months such as after at least 1 year of storage at 25° C./60% RH in diffused daylight.

The present inventors provide herein examples showing that acidic pH values as well as agents belonging to the group of antioxidants and complex binders improve the stability of ipratropium bromide and xylometazoline hydrochloride in aqueous solution. An agent that improves stability according to the present invention is denoted to mean any kind of agent that may inhibit or lessen the degradation of ipratropium or a salt thereof and/or lessen the degradation of xylometazoline or a salt thereof in a composition or in a dosage unit and wherein the degradation may be due to any physical and/or chemical action. Thus, such an agent may prolong the usability and durability of the composition.

As stated, the pH is an important factor, at least in part, in order to achieve a proper shelflife of compositions or dosage units comprising ipratropium or a salt thereof and/or xylometazoline or a salt thereof. Thus, in one embodiment the composition or dosage unit has a pH of at the most pH 7. Preferably, the pH is of at the most pH 6.5, such as of at the most about pH 6, e.g. pH 5.8, even more preferably the pH is of the most about 5.5, pH 5.3 or at the most about pH 5.0. Given that the composition or dosage unit may be administered to a mucosa, in particular a nasal mucosa, the pH need to be suitable for that purpose, such as pH above pH 3, pH 3.5 or even better above pH 4. Thus, despite that the composition or dosage unit may be more stable at pH below 3 or 4, the pH is preferably within a range from about pH 3 to 7. Thus, in some embodiments of the invention, the pH is from about pH 3 to 7, preferably from about pH 4 to 7. In interesting embodiments thereof the pH is from about pH 4 to pH 6.8, such as from pH 4 to pH 6.5, preferably from about pH 4 to 6.2 such as from about pH 4 to 6.0 or pH 4.2 to 5.8. Most preferably the pH is from about pH 4.0 to pH 5.5.

As may be understood, the pH may need to be adjusted in aqueous solutions comprising ipratropium bromide and/or xylometazoline hydrochloride. Thus, suitable embodiments of the invention relate to those, wherein pH is adjusted. Accordingly, compositions, dosage units as well as any aqueous solution comprising ipratropium or a salt thereof and xylometazoline or a salt thereof may further comprise a pH-adjusting agent. The pH-adjusting agent may be any suitable inorganic base, inorganic acid, organic base or organic acid, including acids and bases with one or multiple $pK_a$ values. Typically, an inorganic acid is hydrochloric acid, sulphuric acid, nitric acid, phosphoric acid, hydrobromic acid, hydroiodic acid or hydrofluoric acid, and typically, an organic acid is a water-soluble organic acid, such as formic acid, acetic acid, oxalic acid, propionic acid, citric acid or ascorbic acid. The composition may also comprise mixtures of organic and inorganic acids. Of particular interest are embodiments of the invention wherein the pH-adjusting agent is hydrochloric acid.

In the context of this invention, a suitable effect of an agent is the contribution to achieve a stable pH within a desired limit. As may be understood from the degradation kinetics of ipratropium bromide and/or xylometazoline hydrochloride (se example 1), the degradation increases dramatically when the pH increases. Thus, a minor change in pH may result in much more degradation of the therapeutically active substances, thereby making it difficult to achieve a reliable shelf-life unless the pH is properly controlled. However, due to regulatory rules under the medicinal laws, buffering agents are not allowed in formulations with a pH outside the physiological range that are intended to nasal administration. Therefore, for pharmaceutical use to the nasal mucosa, the composition does not comprise a buffering agent or is essential buffer-free.

Due to the importance of the pH stability, interesting embodiments of the invention relate to compositions, dosage units or any combinations of ipratropium or a salt thereof and xylometazoline or a salt thereof in aqueous solution, wherein said embodiment is stable such that the embodiment does not increase or decrease in pH by more than 0.2 pH units after at least 4 months of storage at 40° C. and 25% RH in darkness.

However, greater tolerances of variability of pH may nonetheless result in stable embodiments, such that the pH should not increase or decrease in pH by more than 1 pH unit, such as not more than 0.5 pH units, preferably not more than 0.4 pH units, such as not more than 0.3 pH units after storage at least 4 months at 40° C. and 25% RH in darkness. As stated, more preferably the pH is not increased or decreased by not more than 0.2 pH units and even more preferably by not more than 0.1 pH units and most preferably by not more than 0.05 pH units after at least 4 months of storage at 40° C. and 25% RH in darkness.

It is shown by the present inventors that very applicable stabilising agents include agents that elsewhere are classified as complex binders. Accordingly, embodiments of this invention include those, wherein the composition or dosage unit further comprises at least one or more complex binder(s). Typical examples of complex binders are those capable of binding inorganic metal ions i.e. alkali metal ions, earth alkali metal ions or heavy metal ions. In specific embodiments of the invention, the complex binder is edetic acid, pentetic acid, nitrilotriacetic acid, malonic acid, succinic acid, glutaric acid, adipic acid, pimelic acid, tartaric acid, malic acid, cortic acid, citric acid and/or their salts. In interesting embodiments thereof, the one or more complex binder(s) is/are edetic acid, its salts and metal complexes; pentetic acid, its salts and metal complexes; nitrilotriacetic acid and its salts; or citric acid and its salts, or mixtures of one or more of said complex binders. Preferably, the complex binder is in the form of a salt, e.g. di-sodium edetate. However, the theory may not be, that the stabilising effect of complex binders is exclusively related to the particular properties of a complex binder of being capable to attach other molecules to it. Therefore, in the context of the present invention, stabilising agents that share the properties of a complex binder to stabilise a combination of ipratropium or a salt thereof as well as xylometazoline or a salt thereof in aqueous solutions are included in preferred embodiments of the invention. In the most preferred embodiment, the complex binder is edetic acid, its salts and metal complexes, preferable edetic acid is in the form of its salts and/or metal complexes, such as disodium edetate.

As stated, antioxidants may also result in a stabilising effect. Accordingly, some embodiments of the invention comprise at least one or more antioxidant(s). Typical examples of antioxidants belong to the group of water soluble vitamins such as ascorbic acid, or they may relate to radical scavengers such as water soluble amino acids (such as cysteine, N,N-dimethylglycine or N-acetyl-cysteine) and flavonoids. In a preferred embodiment, the antioxidant is ascorbic acid.

In the context of the present invention, the stabilising effect may be achieved by each of the above-mentioned factors, pH, complex binders, antioxidants alone or in combination. Thus, interesting embodiments of the invention relate to those comprising a pH in the range of about 4 to 7 and/or one more complex binder(s) and/or one or more antioxidant(s). The pH, complex binders and antioxidants may be similar to those described above.

A further important aspect of the invention relates to a method for stabilising an aqueous solution of ipratropium or a salt thereof and/or xylometazoline or a salt thereof comprising the use of at least one stabilising agent. In one embodiment the stabilising agent is a pH-adjusting agent. In other embodiments the stabiliser is a complex binder and in still other embodiments the stabiliser is anti-oxidants or radical scavengers. In still interesting embodiments the composition comprises at least two stabilising agents, in particular a pH-adjusting agent and a complex binder. Thus, the method for stabilising an aqueous solution of ipratropium or a salt thereof and/or xylometazoline or a salt thereof comprises the step of adding at least one agent selected from the group consisting of pH-adjusting agents, anti-oxidants, radical scavengers and complex binders. In the context of the invention, such pH-adjusting agents, anti-oxidants, radical scavengers and complex binders relate to those mentioned above.

In order to obtain the necessary stabilising effect, the concentration of the at least one excipient capable of acting as a stabilising agent, e.g. a complex binder or a mixture of complex binders is within a certain range. Thus, preferable embodiments according to the invention relates to those, wherein the one or more complex binder(s) and/or one or more antioxidant(s) is/are present in a concentration of about 0.05 mg/ml to 30 mg/ml. Preferably the concentration of the at least one excipient capable of acting as a stabilising agent is of about 0.1 mg/ml to 10 mg/ml, more preferably of about 0.2 mg/ml to 4 mg/ml, even more preferably of about 0.3 to mg/ml to 2 mg/ml, most preferably of about 0.4 mg/ml to 0.8 mg/ml.

Furthermore, the stabilising effect may depend on the proper molar ratio between the stabilising agent, e.g. a complex binder or a mixture of complex binders and ipratropium or a salt thereof. Thus, the one or more complex binder(s) and/or the one or more antioxidant(s) stabilising agent is/are present in a molar ratio relatively to ipratropium or a salt thereof of about 0.0004 to 10, preferably of about 0.01 to 5, more preferably of about 0.1 to 2, even more preferably of about 0.3 to 0.8. Similarly, the stabilising agent is present in a molar ratio relatively to xylometazoline or a salt thereof of about 0.0004 to 10, preferably of about 0.01 to 5, more preferably of about 0.1 to 2, even more preferably of about 0.3 to 0.8.

As stated, a composition as well as a dosage unit comprising ipratropium or a salt thereof and xylometazoline or a salt thereof is in aqueous solution. In the context of this invention, it relates to solutions comprising at least 10% w/w water. However, in preferred embodiments suitable for use with nasal application, the content of water is about at least 95% w/w. However, any content of water above at least 10% w/w is suitable for use, such as at least 20% w/w or, at least 30% w/w. More preferably the content of water is at least 40% w/w, such as at least 50% w/w or at least 60% w/w. Even more preferably the content of water is at least 70% w/w, such as at least 80% w/w or at least 90% w/w. Most preferably the composition comprises at least 95% w/w, such as at least 97% w/w or at least 99% w/w of water. The water suitable for preparing the compositions of this invention may be of any kind and of any chemical purity as well as microbial purity and sterility.

According to the invention suitable salts of ipratropium can be any pharmaceutically acceptable salts. Suitable salts of ipratropium are embodied by ipratropium bromide, ipratropium chloride, ipratropium iodide, ipratropium fluoride or ipratropium hydroxide. However, preferred embodiments of the invention comprise ipratropium bromide.

Xylometazoline is an imidazoline capable of undergoing acid addition salt reaction, whereby the compound becomes ionised and thus becomes more water soluble, which may be advantageous for delivering of drug agents for topical treatment of mucous tissue, including the nasal mucosa. Therefore, a preferred salt of xylometazoline is a xylometazoline acid addition salt. In suitable embodiments the salt may be inorganic or organic. Such acid addition salts may be made of any pharmaceutical acceptable acid, thus resulting in the formation of xylometazoline hydrochloride, xylometazoline hydrobromide, xylometazoline hydroiodide, xylometazoline hydrofluoride, xylometazoline sulphate, xylometazoline nitrate, xylometazoline formate, xylometazoline acetate, xylometazoline citrate, xylometazoline tartrate, or xylometazoline fumarate.

Preferred embodiments of the invention comprise xylometazoline hydrochloride.

According to the invention, other topically active nasal anticholinergic agents may be used in combination with ipratropium or salts thereof including Ephedrine, Phenylephrine, Naphazoline, Oxymethazoline, Tetrahydrozoline, Etaphedrine, Clonazoline, Dimepropione, Fenoxazoline, Indanazoline or salts thereof. Thus, in a further aspect the invention relates to a composition comprising a) ipratropium or a salt thereof; and b) a vasoconstrictor selected from the group consisting of Ephedrine, Phenylephrine, Naphazoline, Oxymethazoline, Tetrahydrozoline, Etaphedrine, Clonazoline, Dimepropione, Fenoxazoline, Indanazoline and salts thereof, in aqueous solution. Preferably, xylometazoline hydrochloride may be replaced by Ephedrine, Phenylephrine, Naphazoline, Oxymethazoline, or salts thereof, e.g. the hydrochloride salt or the hydrobromide salt. The applicable doses that may be used in the combined therapy with ipratropium bromide are those known to be effective in treating nasal congestion by mono-therapy. However, preferably the doses are about half of the usually applied doses in said mono-therapy.

Moreover, alternative anticholinergic agents to ipratropium or a salt thereof may be used in combination with xylometazoline or a salt thereof, such as Oxitropium, Anisotropine, Clidinium, Glycopyrrolate, Mepenzolate or salts thereof. Accordingly, in a still further aspect the invention relates to a composition comprising a) xylometazoline or a salt thereof; and b) an anticholinergic agent selected from the group consisting Oxitropium, Anisotropine, Clidinium, Glycopyrrolate, Mepenzolate and salts thereof, in aqueous solution. In interesting embodiments thereof, the anticholinergic agent is Oxitropium or a salt thereof, such as Oxitropium bromide. The applicable doses that may be used in the combined therapy with xylometazoline or a salt thereof are those known to be effective in treating nasal congestion by mono-therapy.

According to the invention, the amount of the two drug agents in the composition is such that the ipratropium or a salt thereof is present per ml of said composition in an amount of about 0.05 mg to 30 mg, preferably about 0.1 mg to 10 mg, more preferably about 0.15 mg to 5 mg, even more preferably about 0.2 mg to 2 mg, most preferably about 0.3 mg to 1.2 mg.

Xylometazoline or a salt thereof is present pr ml of said composition in an amount of about 0.05 mg to about 30 mg, preferably about 0.2 mg to 10 mg, more preferably about 0.4 mg to 5 mg, even more preferably about 0.5 mg to 2 mg, most preferably about 0.7 mg to 1.5 mg per ml of said composition.

Alternatively, the ipratropium or a salt thereof is present in an amount of about 0.005 to 3%, preferably about 0.01% to 1%, more preferably about 0.015% to 0.5%, even more preferably about 0.02% to 0.2%, most preferably about 0.03% to 0.12% by weight of the composition, and the xylometazoline or a salt thereof is present in an amount of about 0.05% to 30%, preferably about 0.1% to 10%, more preferably about 0.4% to 5%, even more preferably about 0.5% to 2%, most preferably about 0.7% to 1.5% by weight of the composition.

Preferably, the pharmaceutical composition is suitable formulated for administration to a mucosa, preferably a nasal mucosa. According to the invention, a dosage unit is also formulated for mucosal administration, preferably wherein the mucosal administration delivers the active compounds to the nasal mucosa. Suitably formulated is denoted to mean such preparations that a person skilled in the pharmaceutical art may design for administration to a mucosa, and in particular to delivery onto a nasal mucosa.

Thus, especially suitable embodiments of the invention include those further comprising at least one excipient having the ability of adjusting tonicity. Such excipients are sodium chloride or known equivalents to sodium chloride e.g dextrose, various organic acids and their inorganic salts such as boric acid, citric acid, tartaric acid and phosphoric acids. Advantageously, the tonicity is adjusted by mixtures of tonicity adjusting excipients. The resulting solution may have an osmolality in the range of about 100 to 500 mOsm/kg $H_2O$. Preferably, the osmolality is in the range of about 150 to 450 mOsm/kg H2O, more preferably in the range of about 200 to 400 mOsm/kg H2O, still more preferably in the range of about 220 to 350 mOsm/kg H2O. Most suitable, the osmolality is in the range of about 230 to 320 mOsm/kg H2O, such as in the range of about 250 to 300 mOsm/kg H2O.

In still suitable embodiments thereof, the osmolality is in the range of about 260 to 290 such as about 275 mOsm/kg H2O.

As described earlier, administration of ipratropium or salts thereof to a nasal mucosa may result in dehydration of the mucosa. Thus, favourable embodiments of the invention further comprise at least one humectant. Humectants are denoted to pharmaceutically acceptable excipients having the ability of absorbing or retaining moisture such as water. Suitable humectants are mineral oils, vegetable oils, soothing agents, cellulose derivatives, sugars, alcohols, polymers, or membrane conditioners.

Typically humectants according to the invention are sorbitol, propylene glycol, glycerol, glycerine, polyethylene glycols, triacetin, hydroxypropylmethylcellulose methylcellulose, polyvinyl alcohol, polyvinylpyrrolidone, poloxamer. In a particular suitable embodiment of the invention, the humectant is glycerol.

The formulation is advantageously formulated for delivering the active agents from an aqueous solution, wherein the aqueous solution comprises at least 10% of water, and in preferred embodiments the composition is essentially propellant-free. As may be understood, a propellant is poorly miscible with water. Thus, the composition does not comprise a propellant such as a liquid propellant, or is at least essentially free of a liquid propellant, such that the composition comprises less than 5% w/w, preferably less than 1% w/w, more preferably less than 0.5% w/w, most preferably less than 0.1% w/w of said propellant. Furthermore, the choice of excipients, such as humectants is intended to result in a composition, wherein the composition does not form a gel upon administration to the nasal cavity.

Moreover, in suitable embodiments of the invention, the compositions and/or dosage units do not comprise a preservative. For example, benzalkonium chloride may not be suitable for use.

An interesting aspect of the invention relates to a method for the treatment of a condition selected from the group consisting of symptoms associated with the common cold and symptoms associated with rhinitis by administering a combination of therapeutically effective amount of a) a topically active anticholinergic agent, such as ipratropium or a salt thereof; and b) of a topically active vasoconstrictor, such as xylometazoline or a salt thereof, preferably wherein the two agents are dissolved or suspended in aqueous solution. The treatment is preferably directed to a human, but any mammal, such as an animal may also be treated with that combination of a topically active anticholinergic agent and a topically active vasoconstrictor. In further interesting embodiments, the method comprises administering said composition to a child aged at most 15 years, preferably at most 12 years, even more preferably at most 10 years.

In the event, where the composition of ipratropium or a salt thereof and xylometazoline or a salt thereof is formulated into a final medicament ready to use in the treatment or relief of common cold, a further aspect of the invention relates to the use of a combination of a) a topically active anticholinergic agent, such as ipratropium or a salt thereof; and b) of a topically active vasoconstrictor, such as xylometazoline or a salt thereof for the preparation of a medicament, wherein the medicament is formulated for mucosal delivery of an effective amount of ipratropium or a salt thereof and a xylometazoline or a salt thereof for the treatment of conditions selected from the group consisting of symptoms associated with the common cold and symptoms associated with rhinitis.

As can be seen from the examples provided herein, said combination of a topically active anticholinergic agent and a topically active vasoconstrictor may reduce runny nose in a much more effective manner than by administering a topically active vasoconstrictor, only, as exemplified by the combination of ipratropium bromide and xylometazoline hydrochloride.

In the context of the present invention, any suitable topically active vasoconstrictor may be combined with ipratropium or a salt thereof. Likewise, any suitable topically active anticholinergic agent may be used in combination with xylometazoline or a salt thereof. Therefore, in further interesting aspects of the invention, the use or method of treatment relates to the combination of a) ipratropium or a salt thereof; and a vasoconstrictor that may be selected from the group comprising Ephedrine, Phenylephrine, Naphazoline, Oxymethazoline, Tetrahydrozoline, Etaphedrine, Clonazoline, Dimepropione, Fenoxazoline, Indanazoline or salts thereof. Furthermore, another interesting aspect of the invention relates to the combination of a) xylometazoline or a salt thereof; and a topically active anticholinergic agent that may be selected from the group comprising Oxitropium, Anisotropine, Clidinium, Glycopyrrolate, Mepenzolate or salts thereof, In preferred embodiments of the invention, the conditions that are suitable treated are nasal congestion, sneezing and/or hypersecretion (rhinorrea).

Those conditions that are associated with common cold may be caused by viral infection, allergic rhinitis, non-allergic rhinitis and/or perennial rhinitis. However, common cold may also be spontaneously acquired without any further indication of the presence of a viral infection. Rhinitis denotes a condition involving inflammation of the nasal mucosa in response to various stimuli, and may be considered either allergic or non-allergic of seasonal or perennial nature. Perennial rhinitis relates to allergy-mediated rhinitis caused by various allergens, which are present in the environment throughout the year irrespective of the season.

According to the invention, it is advantageous to treat various conditions of common cold by simultaneously, that is to say co-instantaneously, administering an topically active anticholinergic agent, such as ipratropium or a salt thereof, and a topically active vasoconstrictor, such as xylometazoline or a salt thereof, to a nasal mucosa. It may advantageously result in a decrease in severity and duration of e.g. rhinorrhea. The decrease may be observed on the basis of symptom scores, number of nose blowings and/or reduction in weight of secretions.

Moreover, the efficacy of the treatment of symptoms of the common cold may be improved by the simultaneously co-administration of ipratropium or a salt thereof and xylometazoline or a salt thereof, resulting in the need of lower doses of one or each of the two drugs, for example xylometazoline or a salt thereof. Therefore, risk of side effects may be reduced, and it may be more suitable for use in children. Importantly, the combination of the two drug agents into one medicament may improve treatment compliance, due to the reduction of the number of times the patient needs to administer the medicament.

Thus, according to the invention, the administration of a composition of ipratropium or a salt thereof and xylometazoline or a salt thereof is to a mucosa, preferably a nasal mucosa.

The sufficient daily dose for lessening, relieving or curing symptoms of the common cold may vary according to the severity of the common cold as well as the individual need of relief of symptoms in the individual patient. Thus, the daily dose of ipratropium or a salt thereof is equivalent to an amount of about 50 µg to 1500 µg of ipratropium bromide. Typically, the daily dose is equivalent to an amount of about 75 µg to 1100 µg, preferably of about 75 to 900 µg, more preferably of about 100 to 650 µg, most preferably of about 150 to 500 µg such as of about 156 µg, about 312 µg or about 468 µg of ipratropium bromide. Likewise, the sufficient daily dose of xylometazoline or a salt thereof may also vary. The daily dose of xylometazoline or a salt thereof is equivalent of an amount of about 40 µg to 1300 µg of xylometazoline hydrochloride. Preferably, the daily dose is of about 80 to 1100 µg, more preferably of about 100 to 1000 µg, most preferably of about 120 to 800 µg, and typically of about 260 µg, 390 µg, 520 µg or 780 µg of xylometazoline hydrochloride.

Moreover, the proper molar ratio between the two groups of therapeutically active agents, may influence to what extent the symptoms of the common cold may be reduced. Hence, the molar ratio or weighed ratio in a daily dose of ipratropium or a salt thereof in relation to xylometazoline or a salt thereof may be of about 0.2 to 10, such that of about 0.3 to 5, more preferably of about 0.4 to 3, 0.5 to 2, such as 0.6 to 1.5.

For obtaining relief of symptoms of the common cold, it may be important that the nasal mucosa is frequently exposed to the anticholinergic and vasoconstricting agent. Thus, the administration of the above-mentioned topically active anticholinergic and vasoconstricting can be done to one or both nostril(s), one or several times a day, dependent on the severity of the common cold. Preferably, the administration takes place up to three or four times daily in one or both nostril(s).

The typical doses, that may be administered to one or both nostril as well as one or several times a day can also be varied. Thus, upon one administration of ipratropium or a salt thereof to one nostril, an equivalent of about 5 µg to 800 µg of ipratropium bromide, preferably of about 10 µg to 400 µg, more preferably of about 25 to 220 µg, such as of about 39 µg, 78 µg and 156 µg of ipratropium bromide is delivered. Likewise, upon one administration of xylometazoline or a salt thereof to one nostril, an equivalent of about 5 µg to 700 µg of xylometazoline hydrochloride, preferably of about 10 µg to 350 µg, more preferably of about 20 µg to 200 µg, such as of about 32 µg, 65 µg and about 130 µg of xylometazoline hydrochloride, is delivered.

The effective doses of the ipratropium or a salt thereof and xylometazoline or a salt thereof is typically delivered by a dosage unit that delivers a volume of about 10 to 500 µL. However, preferably volumes are those of at most 200 µL, since in the event of nasal administration of volumes exceeding 200 µL there may be a risk of loss of the formulation to the larynx or loss through the nostrils. Thus preferably, the dosage is having a volume of about 10 to 200 µL, most preferably about 50 to 150 µL, such as 130 µL to 140 µL.

According to the invention, the lessening, relief or cure of the symptoms associated with common cold is effected using a combination of ipratropium or a salt thereof and xylometazoline or a salt thereof that are formulated into a stable composition, that have the features described elsewhere in this description. Thus the method of treatment regards the use of a composition according to this invention.

At least one advantageous aspect of the invention is that it may lead to improved treatment of common cold. This is due, at least in part, to the present inventors providing a stable medicament for nasal administration comprising two therapeutic active agents in aqueous solution, whereas such solutions were expected to lead to degradation of the two agents. The medicament is for long-term use and storage. By one single nasal administration of the medicament to one or both nostrils of patients suffering from a common cold, the two agents are delivered simultaneously to the nasal cavity, where they act individually on the sympathetic and cholinergic nerves, resulting in relief of nasal hypersecretion (rhinorrhea) as well as nasal congestion. Hence, a major advantage of the present medicament is related to better treatment compliance due to the reduced number of daily administrations in relation to separate nasal administration of each of the agents.

Another advantage of the present medicament may be a positive synergy between the active agents, resulting in a reduced dosing of one or both of the agents, when compared to separate nasal administration of each one of the agents. Furthermore, the improved treatment, at least in part, is associated with reduced risk of desiccation of the nasal mucosa due to addition of suitable humectants to the medicament. Moreover, the improvement, at least in part, is related to the degree of relief that each individual user of the medicament may experience due to the simultaneously therapeutic action of the two agents, e.g. the individual user may experience that the medicament gives long-term relief of the symptoms of the common cold.

EXAMPLES

Example 1

Stability at Various pH-Conditions

Four compositions were prepared according to the following scheme (Table 1). 0.1M of K-phosphate buffer was added in order to adjust the pH.

TABLE 1

| Ingredients | Concentrations | Compositions | | | |
|---|---|---|---|---|---|
| | | 1 | 2 | 3 | 4 |
| Ipratropium Br | 0.2 mg/ml | + | + | + | + |
| Xylometazoline hydrochloride | 1 mg/ml | + | + | + | + |
| 0.1 M K-phosphate buffer | q.s ad pH | 4.5 | 5.5 | 6.5 | 7.5 |
| Glycerol 85% | 27.3 mg/ml | + | + | + | + |
| Purified H$_2$O | q.s. | + | + | + | + |

Test solutions were filled into glass vials with airtight closures and stored at 40° C./75% RH (relative humidity). Following storage at 0, 1 and 4 months, the content of a major breakdown product of ipratropium bromide, Tropic acid, as well as a major breakdown product of xylometazoline hydrochloride, N-(2-aminoethyl)-2-(4-1,1-dimethylethyl-2,6-dimethylphenyl)-acetamide (NADDA), were quantified using reversed phase HPLC (Xterra RP18 column) with UV detection at 206 nm. A two-solvent gradient was used, with phosphate buffer pH 5.5 as Solvent 1, and with phosphate buffer plus acetonitrile (55:45) adjusted to pH 5.5 as Solvent 2. The resulting retention times of ipratropium bromide and of xylometazoline hydrochloride are of about 12 and 21.5 minutes, respectively. The pH was determined using a pH-meter.

The content of the breakdown products, NADDA and tropic acid as determined in percentage of the initial amount of the parent compound is shown in the following tables 2 and 3.

TABLE 2

| | NADDA (%) | | |
|---|---|---|---|
| | Months of storage | | |
| Composition | 0 | 1 | 4 |
| 1 (pH = 4.5) | 0 | 0 | <0.14 |
| 2 (pH = 5.5) | 0 | <0.14 | 0.3 |
| 3 (pH = 6.5) | 0 | 1.0 | 2.2 |
| 4 (pH = 7.5) | 0 | 6.6 | 13.1 |

TABLE 3

| | Tropic acid (%) | | |
|---|---|---|---|
| | Months of storage | | |
| Composition | 0 | 1 | 4 |
| 1 (pH = 4.5) | 0 | 0.6 | 1.8 |
| 2 (pH = 5.5) | 0 | 3.5 | 9.8 |
| 3 (pH = 6.5) | 0.2 | 26.1 | 59.7 |
| 4 (pH = 7.5) | 0.8 | 94.9 | 100 |

The results show that increasing amounts of both breakdown products are formed upon increasing the pH. In particularly, it is noted that the breakdown of ipratropium bromide is extensive at 40° C., in particularly at pH values close to neutral.

Example 2

Stability of a Composition Comprising pH 4.5 and Na$_2$-EDTA

A composition containing the following ingredients was prepared:

| Ipratropium bromide: | 1.2 mg/ml |
|---|---|
| Xylometazoline hydrochloride: | 1 mg/ml |
| Glycerol 85%: | 2.70% (w/v) |
| Disodium edetate: | 0.5 mg/ml |
| HCl, diluted: | q.s. ad pH 4.5 |
| Purified water: | ad 1 ml |

The composition was placed in brown glass bottles with airtight closure and stored at 40° C./25% RH.

Upon storage for 0, 1.5, 3, 4.5 and 6 months, the content of ipratropium bromide and its breakdown product, Tropic acid, as well as xylometazoline hydrochloride and its breakdown product, N-(2-aminoethyl)-2-(4-1,1-dimethylethyl-2,6-dimethylphenyl)acetamide (NADDA), were quantified using the HPLC method mentioned in Example 1.

Table 4 shows the recovered amount of the parent compounds as well as the percentage of the breakdown products in relation to the initial amount of the parent compounds.

TABLE 4

| | Storage time in months, 40° C./25% RH | | | | |
|---|---|---|---|---|---|
| | 0 | 1.5 | 3 | 4.5 | 6 |
| Ipratropium bromide (IB) | 100% | 98.1% | 100.2% | 98.5% | 98.7% |
| Xylometazoline, HCl | 100% | 100.6% | 101.9% | 99.8% | 101.0% |
| Tropic acid in % of IB | n.d. | 0.5 | 0.9 | 1.6% | 1.9% |
| NADDA in % of Xylometazoline HCl | n.d. | n.d. | n.d. | <0.14% | <0.14% |
| pH | 4.6 | 4.7 | 4.6 | 4.6 | 4.5 |

Example 3

Stability of Compositions Comprising pH 4.5 and/or a Complex Binder

Four compositions comprising either a pH of 4.5, a complex binder or both a pH of 4.5 and a complex binder were prepared according to the following scheme:

TABLE 5

| | | Composition | | | |
|---|---|---|---|---|---|
| Ingredients | Concentrations | 1 | 2 | 3 | 4 |
| Ipratropium Br | 1.2 mg/ml | + | + | + | + |
| Xylometazoline hydrochloride | 1 mg/ml | + | + | + | + |
| Na$_2$EDTA | 0.5 mg/ml | − | + | − | + |
| 0.1 M HCl | q.s ad pH 4.5 | − | − | + | + |
| Purified H$_2$O | q.s. | + | + | + | + |

The compositions were placed at 40° C./nmt 25% RH. After 1, 2, 3, 4, and 6 months of storage, respectively, samples were taken out and analysed for pH, assay and degradation products using the HPLC method mentioned in Example 1.

The content of the stability-indicating degradation products is shown in tables 6 and 7. The content is expressed as the amount of tropic acid and NADDA in percentage of the initial amount of ipratropium bromide and xylometazoline hydrochloride, respectively.

TABLE 6

| | NADDA (%) | | | | |
|---|---|---|---|---|---|
| | Months of storage | | | | |
| Composition | 0 | 1 | 2 | 3 | 4 |
| 1 | nd | nd | 0.05 | nd | 0.08 |
| 2 | nd | nd | 0.03 | nd | 0.06 |
| 3 | nd | nd | 0.03 | nd | 0.04 |
| 4 | nd | nd | 0.02 | nd | 0.04 |

TABLE 7

| | Tropic acid (%) | | | | |
|---|---|---|---|---|---|
| | Months of storage | | | | |
| Composition | 0 | 1 | 2 | 3 | 4 |
| 1 | 0.00 | 0.00 | 1.60 | 1.77 | 1.95 |
| 2 | 0.00 | 0.00 | 1.12 | 1.30 | 1.56 |
| 3 | 0.00 | 0.00 | 0.73 | 0.70 | 0.90 |
| 4 | 0.00 | 0.00 | 0.59 | 0.80 | 0.98 |

The data show that less of the stability-indicating degradation products are formed in compositions comprising a pH of 4.5 and/or disodium edetate. After 4 months of storage at 40° C., the compositions 2, 3, and 4 clearly comprises less of the degradation products. Thus indicating that those compositions comprising an agent for adjusting the pH to a slightly acidic pH and/or comprising a complex binder possesses superior stability to the composition 1, wherein no complex binder or pH-adjusting agent has been added.

Example 4

Stability of Compositions Comprising Varying Complex Binders or Antioxidants

A number of different agents were tested for their stabilising effects in compositions comprising ipratropium bromide and xylometazoline hydrochloride.

A basic composition was prepared such that upon adding further agents, the final concentration of each of the active ingredients and excipients were as follows:
  0.6 mg/ml ipratropium bromide
  1.0 mg/ml xylometazoline hydrochloride
  27.3 mg/ml glycerol 85%
  dissolved in purified water.
One of the following agents were added:
  0.125 mg/ml disodium edetate
  0.125 mg/ml calcium dinatrium edetate
  0.125 mg/ml dipotassium edetate
  0.125 mg/ml trisodium edetate
  Ad pH 4.5 with ascorbic acid
  Ad pH 4.5 with citric acid
To those compositions, which were not pH-adjusted with the agent itself (i.e. with ascorbic acid and citric acid), 0.1M HCl was added ad pH 4.5. The formulations were stored at 40° C./75% RH and samples were analysed after 4 months of storage. Assay and content of degradation products were analysed by the HPLC method mentioned in example 1, pH was measured using a pH-meter.

Results are shown as the recovered amount of xylometazoline hydrochloride and ipratropium bromide in percentage of their initial amount. Concerning the content of the degradation products, it is shown in percentage of the initial amount of their parent compounds.

TABLE 8

| Additives | Xylometazoline hydrochloride (%) | Ipratropium bromide (%) | NADDA (%) | Tropic acid (%) |
|---|---|---|---|---|
| Reference | 98.37 | 96.11 | 0.10 | 3.63 |
| Na₂EDTA | 98.42 | 98.28 | 0.02 | 1.13 |
| CaNa₂EDTA | 98.68 | 98.77 | 0.03 | 1.09 |
| K₂EDTA | 98.26 | 98.24 | 0.04 | 1.28 |
| Ascorbic acid | 98.49 | 98.35 | 0.05 | 1.30 |
| Citric acid | 98.72 | 98.16 | 0.04 | 1.66 |

The results in Table 8 show a clearly inhibition in the formation of breakdown products of both xylometazoline hydrochloride and ipratropium bromide upon adding the above-mentioned agents to the basic composition. The reference consists of the basic composition with 0.1M HCl added ad pH 4.5. In particularly, the added agents significantly inhibited the degradation of ipratropium bromide. Thus, compositions comprising edetate salts, ascorbic acid, or citric acid have improved stability.

Example 5

Stability of Compositions Comprising Other Vasoconstricting Agents in Combination with Ipratropium Bromide Compositions comprising vasoconstricting agents alternative to xylometazoline such as ephedrine and oxymethazoline were prepared according to the following scheme:

TABLE 9

| Composition | 1 | 2 | 3 | 4 |
|---|---|---|---|---|
| Ipratropium bromide, 0.6 mg/ml | x | x | x | x |
| Glycerol, 27.3 mg/ml 85% | x | x | x | x |
| Na₂EDTA, 0.5 mg/ml | x | x | | |
| Purified water | x | x | x | x |
| HCl q.s. ad 4.5 | x | x | x | x |
| Ephedrine HCl, 10.0 mg/ml | x | | x | |
| Oxymetazoline, 0.5 mg/ml | | x | | x |

The formulations were placed in closed glass vials, clear, and stored at 40° C./75% RH and 60° C./humidity, respectively. Samples were assayed for content of the parent compounds and degradation products by HPLC. Ipratropium bromide, ephedrine and impurities were determined by the HPLC method described in Example 1. Oxymetazoline was analysed by reversed-phase HPLC using a Waters Symmetry C18 column and a UV detector at 220 nm. The method was isocratic using a mixture of phosphate buffer, triethanolamine and acetonitrile as the mobile phase.

The content of ephedrine and oxymetazoline, respectively, in percentage of the initial content are shown in table 10. The amount of tropic acid in percentage of the initial amount of ipratropium bromide is shown in table 11.

TABLE 10

| | Composition | 1 month 60° C. | 4 months 60° C. | 4 months 40° C. |
|---|---|---|---|---|
| Ephedrine (%) | 1 | 98.5 | 100.2 | 99.9 |
| Oxymetazoline (%) | 2 | 100.7 | 98.2 | 100.4 |

These stability data clearly show that compositions comprising ephedrine and oxymethazoline, respectively, are stable upon storage at accelerated conditions.

TABLE 11

| Tropic acid (%) | Composition | 1 month 60° C. | 4 months 60° C. | 4 months 40° C. |
|---|---|---|---|---|
| IB + ephedrin | 3 | n.a. | 15.15 | 5.57 |
| IB + ephedrin + Na₂EDTA | 1 | n.a. | 11.31 | 0 |
| IB + oxymetazolin | 4 | 7.27 | n.a | 2.49 |
| IB + oxymetazolin + Na₂EDTA | 2 | 4.64 | n.a | 1.53 |

From these results, it appears that the degradation of ipratropium bromide to tropic acid is reduced or inhibited in compositions comprising disodium edetate, thus clearly indicating a stabilising effect of edetate salts on ipratropium bromide.

Example 6

Compositions Comprising Various Humectants

The following active substances and excipients were used for preparing various compositions:

| I | Ipratropium bromide | 0.05 to 30 mg |
|---|---|---|
| II | Xylometazolin HCl | 0.05 to 30 mg |
| III | Disodium edetate | 0 to 10 mg |
| IV | Humectants | 0 to 50 mg |
| V | Other excipients | 0 to 50 mg |
| VI | Hydrochloric acid/sodium hydroxide, dilute | q.s (pH 4.0-7.0) |
| VII | Purified water | ad 1 ml |

The excipients of group IV (humectants) may be present individually or in combination in the composition. Preferred excipients of group IV are those excipients or combination of excipients that reduces/reduce the irritation of the nasal mucosa upon administering the compositions. Excipients with any chemical or microbial quality are suitable for use in the above-mentioned examples. Examples of excipients of group IV are, but not limited to:

Cellulose Derivatives:
Hydroxypropylmethylcellulose, sodium carboxymethylcellulose, microcrystalline cellulose, methylcellulose, hydroxypropylcellulose, hydroxyethylcellulose.

Sugars:
Glucose, glucose anhydrate, sorbitol, mannitol, glycerol/glycerin, triacetin (1,2,3-Propanetriol triacetate), dextran 70.

Alcohols:
Propylene glycol, polyethyleneglycol 400 or polyethyleneglycol 300, polyvinyl alcohol octoxynol (ethoxylated alkylphenol).

Polymers:
Polyvinylpyrrolidone, carbomer, tyloxapol, poloxamer (α-Hydro-ωhydroxypoly(oxyethylene)poly(oxypropylene) poly(oxyethylene) block copolymer).

Oils:
Mineral oil, vegetable oil.

Others:
soothing agents, membrane conditioners, trometamol.

The formulation may comprise other pharmaceutically acceptable excipients (group V excipients) known to the person skilled in the art, such as tonicity regulators (e.g. sodium chloride, glycerol, glycerin, sorbitol, propylene glycol and polyethylene glycol), substances which improve the organoleptic properties of the formulation (e.g. sweeteners, menthol and aromatic substances) and preservatives (e.g benzalconium chloride, benzyl alcohol, parabens, mercury salts, phenols). The excipients of group V may be present individually or in combination in the composition.

The most preferred amounts of active substances and excipients in the various formulations are as follows:

| | | |
|---|---|---|
| I | Ipratropium bromid | 0.3 to 1.2 mg |
| II | Xylometazoline hydrochloride | 1 mg |
| III | Disodium edetate | 0.5 mg |
| IV | Humectants | 27-27.5 mg of glycerol 85% |
| V | Hydrochloric acid, dilute | q.s (ad pH 4.5) |
| VI | Purified water | ad 1 ml |

Procedure:

Ipratropium bromide, xylometazoline hydrochloride, disodium edetate and the one or more humectant according to table 12 were weighed and mixed on a magnetic stirrer with approximately 480 ml distilled water. 0.1M HCl was added dropwise until pH 4.5, and distilled water was then added ad 500 ml. The preparation was left constantly stirred by a magnetic stirrer until the solid agents were dissolved, and then filtered through a 0.45 µm filter.

The following ingredients were present in all compositions and the humectants of table 12 were further added to give individually different compositions:

| | |
|---|---|
| Ipratropium bromide: | 600 mg |
| Xylometazoline hydrochloride: | 500 mg |
| Disodium edetate: | 250 mg |
| 0.1M HCl: | ad pH 4.5 |
| Distilled water: | Ad 500 ml |

TABLE 12

| Composition | Sodium chloride (g) | Sorbitol (g) | Propylene glycol (g) | Glycerol 85% (g) | Hydroxypropyl methylcellulose (g) |
|---|---|---|---|---|---|
| C | 4.3 | | | | |
| D | | 27 | | | |
| E | | | 9.5 | | |
| F | | | | 12 | |
| H | | | | | 10 |
| I | | 8 | 2.8 | | |
| J | | 8 | | 3.6 | |
| L | | 5.3 | 1.9 | 2.4 | |

Example 7

Stability Testing of Compositions Comprising Varying Humectants

Long-term stability of a number of compositions comprising the two active substances (ipratropium bromide and xylometazoline hydrochloride), disodium edetate and various humectants were carried out.

Stability Testing

Compositions C to L were filled into glass vessels and closed with airtight closure and stored at 25° C./60% RH in the dark and at 40° C./25% RH in the dark.

Samples were taken out at time 0, 3, 6 and 9 months and analysed quantitatively for the content of ipratropium bromide and xylometazoline hydrochloride as well as their major breakdown products, see Example 1.

Results

All the compositions C-L were clear like water during the 9 months of storage.

The content of both active substances ipratropium bromide and xylometazoline hydrochloride are essentially unchanged after 2 months of storage at 25° C. and 60% RH or at 40° C. and max. 25% RH, respectively. Furthermore, the compositions C to H were also stable upon storage for a longer period at similar conditions. Data for compositions I-L are missing. Also, the pH is essentially constant during storage (see tables 13 to 18).

TABLE 13

Ipratropium bromide (% w/w of initial content)
Storage: 25° C. and 60% RH

| | Months of storage | | | | | |
|---|---|---|---|---|---|---|
| Formulation | 0 | 0.5 | 1 | 2 | 5 | 9 |
| C | 100 | 100.4 | 99.6 | 100.2 | 100.4 | 99.5 |
| D | 100 | 100.4 | 100.0 | 100.3 | 100.5 | 98.5 |
| E | 100 | 99.9 | 100.1 | 100.2 | 100.6 | 100.0 |
| F | 100 | 100.4 | 100.0 | 100.6 | 100.4 | 99.7 |
| H | 100 | 100.8 | 101.6 | 101.2 | 102.0 | 101.7 |
| I | 100 | 100.3 | 100.5 | 100.0 | — | — |
| J | 100 | 100.2 | 100.2 | 100.3 | — | — |
| L | 100 | 100.0 | 100.5 | 100.0 | — | — |

TABLE 14

Ipratropium bromide (% w/w of initial content)
Storage: 40° C. and max 25% RH

| | Months of storage | | | | | |
|---|---|---|---|---|---|---|
| Formulation | 0 | 0.5 | 1 | 2 | 5 | 9 |
| C | 100 | 100.2 | 99.3 | 99.6 | 99.1 | 97.4 |
| D | 100 | 100.6 | 99.7 | 99.9 | 98.8 | 97.3 |
| E | 100 | 100.0 | 99.7 | 99.8 | 98.6 | 97.0 |
| F | 100 | 99.8 | 99.9 | 99.6 | 98.3 | 97.1 |
| H | 100 | 101.3 | 101.0 | 100.5 | 98.0 | 98.1 |
| I | 100 | 100.2 | 100.6 | 100.5 | — | — |
| J | 100 | 100.1 | 103.9 | 100.0 | — | — |
| L | 100 | 100.0 | 100.1 | 100.2 | — | — |

TABLE 15

Xylometazoline hydrochloride (% w/w of initial content)
Storage: 25° C. and 60% RH

| Formulation | Months of storage | | | | | |
|---|---|---|---|---|---|---|
| | 0 | 0.5 | 1 | 2 | 5 | 9 |
| C | 100 | 100.5 | 99.9 | 100.7 | 101.6 | 100.0 |
| D | 100 | 100.1 | 100.0 | 100.3 | 101.3 | 99.1 |
| E | 100 | 100.1 | 100.3 | 100.5 | 101.7 | 99.7 |
| F | 100 | 100.5 | 100.4 | 100.9 | 101.7 | 100.3 |
| H | 100 | 99.8 | 100.7 | 100.3 | 102.6 | 100.8 |
| I | 100 | 100.9 | 101.7 | 100.6 | — | — |
| J | 100 | 100.9 | 101.5 | 100.7 | — | — |
| L | 100 | 100.5 | 101.7 | 100.2 | — | — |

TABLE 16

Xylometazoline hydrochloride (% w/w of initial content)
Storage: 40° C. and max. 25% RH

| Formulation | Months of storage | | | | | |
|---|---|---|---|---|---|---|
| | 0 | 0.5 | 1 | 2 | 5 | 9 |
| C | 100 | 100.4 | 99.9 | 100.8 | 101.4 | 100.0 |
| D | 100 | 100.1 | 100.1 | 100.5 | 101.4 | 100.1 |
| E | 100 | 99.9 | 100.2 | 100.7 | 101.4 | 100.0 |
| F | 100 | 100.5 | 100.4 | 100.7 | 101.7 | 100.3 |
| H | 100 | 100.3 | 100.6 | 100.0 | 99.5 | 99.7 |
| I | 100 | 101.2 | 102.1 | 101.5 | — | — |
| J | 100 | 101.0 | 105.4 | 100.9 | — | — |
| L | 100 | 100.7 | 101.8 | 101.3 | — | — |

TABLE 17 pH
Storage: 25° C. and 40% RH

| Formulation | Months of storage | | | | | |
|---|---|---|---|---|---|---|
| | 0 | 0.5 | 1 | 2 | 5 | 9 |
| C | 4.40 | 4.48 | 4.67 | 4.52 | 4.57 | 4.57 |
| D | 4.48 | 4.52 | 4.56 | 4.57 | 4.57 | 4.57 |
| E | 4.50 | 4.54 | 4.54 | 4.62 | 4.61 | 4.65 |
| F | 4.55 | 4.60 | 4.65 | 4.69 | 4.72 | 4.73 |
| H | 4.42 | 4.43 | 4.43 | 4.41 | 4.42 | 4.36 |
| I | 4.55 | 4.58 | 4.59 | 4.59 | — | — |
| J | 4.54 | 4.59 | 4.59 | 4.60 | — | — |
| L | 4.53 | 4.59 | 4.60 | 4.60 | — | — |

TABLE 18 pH
Storage: 40° C. and max. 25% RH

| Formulation | Months of storage | | | | | |
|---|---|---|---|---|---|---|
| | 0 | 0.5 | 1 | 2 | 5 | 9 |
| C | 4.40 | 4.51 | 4.58 | 4.56 | 4.64 | 4.66 |
| D | 4.48 | 4.55 | 4.61 | 4.60 | 4.60 | 4.52 |
| E | 4.50 | 4.62 | 4.61 | 4.65 | 4.64 | 4.59 |
| F | 4.55 | 4.68 | 4.70 | 4.70 | 4.69 | 4.60 |
| H | 4.42 | 4.47 | 4.40 | 4.38 | 4.38 | 4.35 |
| I | 4.55 | 4.58 | 4.60 | 4.53 | — | — |
| J | 4.54 | 4.57 | 4.59 | 4.53 | — | — |
| L | 4.53 | 4.57 | 4.58 | 4.53 | — | — |

Example 8

Clinical Efficacy and Safety with Various Doses of Ipratropium Bromide

Purpose:

A double-blind, randomised, clinical dose-finding trial to evaluate the efficacy and safety of a combination of xylometazoline hydrochloride and ipratropium bromide in the treatment of nasal symptoms of common cold. The effect and safety is compared upon treatment with Zymelin® nasal spray that comprises xylometazoline hydrochloride as the only active substance.

Trial Design:

Double-blind, controlled, randomised, parallel group, phase II trial with four treatment arms. The control group will receive xylometazoline hydrochloride. The treatment groups will receive the same dose of xylometazoline hydrochloride as the control group and in addition ipratropium bromide in one of three doses. The duration of each treatment is at least 2×24 hours, after which the subjects can continue treatment as necessary for an additional 2×24 hours period. Visit 2 will take place Day 8, 9 or 10 after initiation of test treatment.

Subjects will be evenly distributed between test treatments. Subjects will be stratified according to score of runny nose at screening, i.e. two strata: one with the score 2 (moderate), the other with the score 3 (severe).

Treatment

A: 1.2 mg/ml ipratropium bromide+1 mg/ml xylometazoline hydrochloride

B: 0.6 mg/ml ipratropium bromide+1 mg/ml xylometazoline hydrochloride

C: 0.3 mg/ml ipratropium bromide+1 mg/ml xylometazoline hydrochloride

D: 1 mg/ml xylometazoline hydrochloride (Zymelin®)

Inclusion Criteria

The most important inclusion criteria relates to:
1. Age between 18 and 65 years
2. A history of common cold symptoms for no longer than 48 hours
3. A score at screening of at least moderate (2) on a 4-point scale for the symptom runny nose within the latest 24 hours
4. A score at screening of at least mild (1) on a 4-point scale for the symptom nasal congestion within the latest 24 hours Exclusion Criteria For inclusion all exclusion criteria must be answered "no".
1. Known hypersensitivity to xylometazoline hydrochloride or ipratropium bromide
2. Participation in another drug trial within one month prior to the beginning of this trial
3. Significant cardiovascular, renal, hepatic, endocrine, metabolic, neurologic, pulmonary, psychiatric or other systemic disease
4. Perennial or allergic rhinitis caused by allergen in season
5. Nasal polyps or other significant nasal abnormalities
6. Glaucoma
7. Prostate hypertrophy
8. Frequent complications associated with upper respiratory infections such as sinusitis or bronchitis
9. Pregnancy or breast feeding
10. Any history of Rhinitis Medicamentosa
11. Use of nasal anti-congestion or anti-secretion medication within 1 week prior to signing the Informed Consent Document 12. Use of monoamine oxidase inhibitors (MAOI) within 1 month prior to signing the Informed Consent Document
13. Any patient developing rhinitis that requires medical attention
14. Participation in sport activities during the treatment period.

Trial Products

The combination of ipratropium bromide and xylometazoline hydrochloride is delivered in a nasal multiple dose preservative free device. The device consists of a glass bottle (19 ml), a non-vented pump with a nominal volume of 130 µl and an actuator. This combination of glass bottle, pump and actuator, and a filling volume of 10 ml delivers 130 µl±10% per puff and approximately 70 doses per device.

The formulation of the combination of xylometazoline hydrochloride and ipratropium bromide in three varying concentrations as well as the formulation of the control drug (xylometazoline hydrochloride alone) is described below:

| Formulations | A | B | C | D |
|---|---|---|---|---|
| Xylometazoline hydrochloride (mg/ml) | 1.0 | 1.0 | 1.0 | 1.0 |
| Ipratropium bromide (mg/ml) | 1.2 | 0.6 | 0.3 | 0 |
| Disodium edetate, glycerol and hydrochloric acid/sodium hydroxide ad pH 4.5. | For concentrations, see Example 2. | | | * |

* Formulation D is the product Zymelin, which has a pH of 5.5 and no content of glycerol.

Assessments:

Day 1. Subjects eligible for the trial in terms of common cold symptoms must have a score of minimum 2 for runny nose and a score of minimum 1 for blocked nose within the latest 24 hours. The subjects score from a 4-point scale the subjective feeling of the following common cold symptoms (runny nose; blocked nose; cough; sore throat; headache). The scale is graded the following way:

Score 0: absent symptoms (no sign/symptom evident)
Score 1: mild symptoms (sign/symptom clearly present, but minimal awareness; easily tolerated)
Score 2: moderate symptoms (definite awareness of sign/symptom that is bothersome but tolerable)
Score 3: severe symptoms (sign/symptom that is hard to tolerate; causes interference with activities of daily living and/or sleeping).

Primary efficacy endpoint is: change in nasal secretion during the first 24-hour period after initiation of test treatment measured by the number of paper tissues used in that period. Secondary efficacy endpoints are: 1) change in nasal secretion during the second 24-hour period after initiation of test treatment measured by the number of paper tissues used in that period, 2) subjective daily evaluation of nasal secretion recorded during treatment and 3) subjective daily evaluation of nasal congestion recorded during treatment. Safety endpoints are heart rate, blood pressure and alertness. Adverse events will be recorded from screening to "End of trial visit". Each safety endpoint is assessed at baseline at visit 1 prior to the first dose, 30 min and 60 min after the first dose and a baseline recording is repeated at visit 2.

Drug administration. Subjects are instructed to self-administer trial medication three times daily with 6 hours intervals; once in the morning at 08.00±3 hours, once in the afternoon at 14.00±3 hours and once in the evening at 20.00±3 hours for at least 2×24 hours following the first dose. Furthermore, subjects are told that they are allowed to continue treatment as necessary for an additional 2×24 hours period Registration of paper tissues used. The registration of paper tissues used is initiated momentarily after administration of the first dose of medication. The exact time of initiation of test treatment is noted in the CRF and in the subject diary.

Subjects are carefully instructed to only blow their nose once in each paper tissue. One tissue should be used for both nostrils. Subjects are instructed in the use of paper tissues during the first and second 24 hours period, respectively.

Safety endpoints are assessed including measurement of heart rate, blood pressure and alertness at 30 min and 60 min after administration of the first dose.

Self assessment. Subjects are instructed to score the perceived nasal secretion and nasal congestion on a home basis in the period when administrating test treatment, i.e. 2-4 days. These scores are carried out as reflective symptom scores, i.e. at least the first 2 days at the same time point as the time for administration of the first dose and prior to administering the next dose, thus evaluating overall symptom severity in each 2×24 hour period. Also instantaneous scores are assessed, i.e. immediately before each dose and 3 hours following each dose, thus evaluating symptom severity around each dosing interval. Symptoms are evaluated using the 4-point scale and are recorded in the diary.

Day 2-3

Drug administered. Subjects self-administer the test treatment TID as instructed by the Investigator. Drug administration includes 3 daily doses in each nostril for all subjects within the first 2×24 hours period of treatment administered in the morning, afternoon and evening with 6 hours intervals. After this period, subjects are allowed to continue treatment as necessary for an additional 2×24 hours period.

Registration of used paper tissues. All unused paper tissues for the first and second 24-hours periods use are kept separate for return at Visit 2 and are registered in the CRF at visit 2.

Self assessment. Subjects score the perceived nasal secretion and nasal congestion on a home basis in the period when administrating test treatment. These scores are carried out as reflective symptom scores, i.e. at least every first two days at the same time point as the time for administration of the first dose and prior to administering the next dose, and as instantaneous scores, i.e. immediately before each dose and 3 hours following each dose, thus evaluating symptom severity around each dosing interval. Symptoms are evaluated using the 4-point scale and are recorded in the diary.

Adverse events. Any adverse events are noted in the diary.

Day 4-5

Drug administered. If necessary (symptoms still present) subjects self-administer test treatment TID until the 4th 24 hours period on Day 5. Test treatment is thus terminated fulfilling the 4×24 hours period of trial medication.

Self assessment. If treatment is taken on Day 4 and 5 subjects score the perceived nasal secretion and nasal congestion on a home basis. These scores are carried out as reflective symptom scores at the same time point as the time for administration of the first dose and prior to administering the next dose, and as instantaneous scores, i.e. immediately before each dose and 3 hours following each dose, thus evaluating symptom severity around each dosing interval. Symptoms are evaluated using the 4-point scale and are recorded in the diary.

Visit 2/Day 8-10

The subjects report to the clinic and bring back the remaining trial medication, unused paper tissues and the completed diary. The concomitant medication and adverse event pages are completed. Nasal and physical examination including vital signs and safety (heart rate, blood pressure, and alertness) are performed. The Investigator fills in the drug accountability form.

Results:

Nasal secretion for days 1 and 2 is shown in table 19 and subjective evaluation of runny nose and nasal congestion is shown in table 20.

TABLE 19

Number of nose blows in the treatment groups at days 1 and 2 (PP)

|   | Treatment | N | Mean | Min. | Max. | p-value |
|---|---|---|---|---|---|---|
| 1 | Ipra 0.0 (D) | 47 | 38 | 6 | 150 | — |
|   | Ipra 0.3 (C) | 42 | 35 | 10 | 90 | 0.89 |
|   | Ipra 0.6 (B) | 47 | 26 | 2 | 134 | 0.03 |
|   | Ipra 1.2 (A) | 44 | 28 | 4 | 90 | 0.14 |
| 2 | Ipra 0.0 (D) | 47 | 24 | 2 | 96 | — |
|   | Ipra 0.3 (C) | 42 | 20 | 0 | 64 | 0.60 |
|   | Ipra 0.6 (B) | 47 | 17 | 2 | 81 | 0.23 |
|   | Ipra 1.2 (A) | 44 | 20 | 3 | 84 | 0.57 |

N = Number of patients

The primary endpoint, i.e. the mean number of nose blows during the first 24 hours, was 38 for ipra 0.0 and 35, 26 and 28 for ipra 0.3, 0.6 and 1.2, respectively. The result for ipra 0.6 was significant (p=0.03). The secondary endpoint: Mean number of nose blows during the second 24 hours did not differ between treatment groups; it was reduced by approx. ⅓ compared to day 1.

TABLE 20

Mean subjective score of runny nose and nasal congestion (ITT)

| Day | Treatment | N | Runny nose (mean) | Nasal congestion (mean) |
|---|---|---|---|---|
| 1 | Ipra 0.0 (D) | 47 | 1.7 | 1.3 |
|   | Ipra 0.3 (C) | 44 | 1.6 | 1.4 |
|   | Ipra 0.6 (B) | 47 | 1.5 | 1.6 |
|   | Ipra 1.2 (A) | 44 | 1.4 | 1.4 |
| 2 | Ipra 0.0 (D) | 47 | 1.1 | 0.9 |
|   | Ipra 0.3 (C) | 44 | 1.2 | 1.1 |
|   | Ipra 0.6 (B) | 47 | 0.9 | 1.1 |
|   | Ipra 1.2 (A) | 44 | 0.9 | 0.9 |
| 1 + 2 | Ipra 0.0 (D) | 47 | 2.9 | 2.3 |
|   | Ipra 0.3 (C) | 44 | 2.9 | 2.6 |
|   | Ipra 0.6 (B) | 47 | 2.4 | 2.8 |
|   | Ipra 1.2 (A) | 44 | 2.4 | 2.4 |

N = Number of patients

The mean sum of subjective scores for runny nose at days 1+2 was 2.4 for ipra 0.6 and ipra 1.2 compared to 2.9 for ipra 0.0 (p=0.07). The mean sum of subjective scores for congestion at days 1+2 varied between 2.3 and 2.8; the lowest value was seen for ipra 0.0. The scores (0-3) for the two symptoms were also distributed according to patients (%). It appears that runny nose was reduced by the addition of ipratropium to xylometazoline.

Display of Adverse Events

The adverse events that occurred in more than 1%, i.e. in two or more patients are shown in table 21.

TABLE 21

Adverse events with a rate of occurrence >1%

| | Ipra 0.0 (D) N = 48/47 | | | Ipra 0.3 (C) N = 45/44 | | | Ipra 0.6 (B) N = 47 | | | Ipra 1.2 (A) N = 45 | | | |
|---|---|---|---|---|---|---|---|---|---|---|---|---|---|
| Preferred Term | n | (%) | E | n | (%) | E | n | (%) | E | n | (%) | E | Total |
| Nasal irritation | 3 | 6.3 | 3 | | | | | | | 3 | 6.7 | 3 | 6 |
| Nasal burning | 1 | 2.1 | 1 | | | | | | | 1 | 2.2 | 1 | 2 |

N = Number of patients; n = Number of patients with event; % = Number of patients with event of all patients (%); E = Number of adverse events As can be seen from Table 21, sensation of nasal irritation and nasal burning is experienced in patients receiving the formulation with high content of ipratropium bromide (formulation A) or by the formulation comprising xylometazoline hydrochloride (formulation D), only. It may be noted that the formulation D does not comprise a humectant that may decrease nasal irritation.

Example 9

Test Model for Investigating the Clinical Efficacy and Safety of Compositions Comprising Varying Amounts of Xylometazoline Hydrochloride A double-blind and randomised trial evaluating the efficacy and safety of two combinations of ipratropium and xylometazoline, namely 0.6 mg/ml ipratropium bromide combined with 0.5 mg/ml xylometazoline hydrochloride (low) and 0.6 mg/ml ipratropium bromide combined with 1.0 mg/ml xylometazoline hydrochloride (high), in comparison to formulations comprising only one of the active substances (formulation comprising ipratropium bromide 0.6 mg/ml and a formulation comprising xylometazoline hydrochloride 1.0 mg/ml (Zymelin®)) and also in comparison to a placebo (formulated in accordance to Example 2, but without therapeutically active substances added) for nasal symptoms of common cold.

Trial Design:

Double-blind, randomised, parallel group, trial with two fixed-dose combinations of ipratropium and xylometazoline, Zymelin® and placebo as described above. Test treatment must be taken three times daily for 24 hours and thereafter until disappearance of rhinorrhea and nasal congestion but no longer than 7 days. Subjects will fill in a diary for 9, 10 or 11 days. Subjects will score their subjective evaluation of runny nose, nasal congestion, and general impression during treatment and note any adverse events from randomisation to End-of-trial in a diary. Subjects will be evenly distributed between the five treatment groups.

Trial Population:

Male or female subjects 18 years or above with symptoms of common cold but otherwise healthy.

Assessments:

Primary efficacy endpoints are:
Subjective rhinorrhea score on a 4-point rating scale based on an overall score after the first 24-hour period.

Subjective nasal congestion score on a 4-point rating scale based on an overall score after the first 24-hour period.

Secondary efficacy endpoints are:

Subjective rhinorrhea score based on overall scores after each 24-hour period during treatment.

Subjective nasal congestion score based on overall scores after each 24-hour period during treatment.

Rhinorrhea measured by the number of paper tissues used in each 24-hour period during treatment.

Composite rhinorrhea and nasal congestion score based on overall scores after each 24-hour period during treatment.

General impression score on a 5-point rating scale after the first 24-hour period and at End-of-trial.

Safety endpoints are:

Adverse events recorded from the subject signed the Informed Consent Form and until the End-of-trial visit and followed up if necessary.

Test Treatment:

Test treatments are delivered as aqueous solutions in nasal spray bottles. The five treatment groups receive one of two combinations of ipratropium (0.6 mg/ml) and xylometazoline (0.5 mg/ml ("Low") or 1.0 mg/ml ("High")), ipratropium, Zymelin® or placebo as shown in the table below. The dosage is one spray per nostril three times daily for 24 hours and thereafter until the disappearance of rhinorrhea and nasal congestion but no longer than 7 days. All formulations except Zymelin® contain disodium edetate, glycerol and hydrochloric acid/sodium hydroxide, with pH 4.5. Zymelin® contains sodium edetate, disodium phosphate, sodium dihydrogen phosphate, and sodium chloride. The concentrations and doses of the formulations are listed below.

| Test treatment | "High" | "Low" | Ipratropium bromide | (Zymelin ®) | Placebo |
|---|---|---|---|---|---|
| ipratropium bromide, mg/ml | 0.6 | 0.6 | 0.6 | 0.0 | 0.0 |
| xylometazoline, mg/ml | 1.0 | 0.5 | 0.0 | 1.0 | 0.0 |
| ipratropium, ug per spray | 78 | 78 | 78 | 0 | 0 |
| xylometazoline, ug per spray | 130 | 65 | 0 | 130 | 0 |

Inclusion Criteria and Exclusion Criteria as in Example 8.

Visit 1/Day 1/After Randomisation

Test treatment. The subject receives one nasal spray bottle according to randomisation, a diary and 1×150, 1×100, 3×50 and 2×30 paper tissues—labelled 'Day 1' to 'Day 7'. The subject takes the first test treatment dose under supervision and the exact time is noted in the CRF and the diary.

Use of paper tissues is started as soon as needed after administration of the first test dose. Subjects are instructed not to wipe their nose. They must blow their nose only once in each paper tissue that should be used for both nostrils. Unused paper tissues for each 24-hour period must be kept separately for return at visit 2

Self assessment. Subjects are instructed to score rhinorrhea and nasal congestion as long as test treatment is taken. This must be done immediately before and 3 hours after each dose. An overall score is done after each 24-hour period. General impression of test treatment is scored after the first 24-hour period and at End-of-trial.

Adverse events. The subjects are instructed to record all adverse events in the diary from the Informed Consent Form was signed until the End-of-trial.

Days 2-7

Test treatment must be taken for 24 hours and thereafter until the disappearance of both rhinorrhea and nasal congestion but no longer than 7 days.

The time of intake and assessments of rhinorrhea and nasal congestion for the first 24 hours must be copied for the following 24-hour periods.

Day 8

Subjects must continue recording of any concomitant medication and adverse events.

During the Trial

Subjects are instructed to self-administer test treatment three times daily with 6-hour intervals, i.e. in the morning at 08.00±3 h, in the afternoon at 14.00±3 h and in the evening at 20.00±3 h. Subjective evaluation of rhinorrhea and nasal congestion must be scored immediately before and 3 hours after each dose as long as test treatment is used. In addition, an overall scoring of rhinorrhea and nasal congestion must be done after each 24-hour period. Use of test treatment is to be stopped when both symptoms of rhinorrhea and nasal congestion have disappeared. The actual time of disappearance of rhinorrhea and nasal congestion is to be evaluated subjectively.

General impression of test treatment must be scored on a categorical 5-point rating scale (1=poor, 2=fair, 3=good, 4=very good, and 5=excellent) after the first 24-hour period and at End-of-trial (28).

Instructions for Use

Test treatment is taken as one spray in each nostril three times daily

Adverse Event (AE)

An AE is any untoward medical occurrence in a clinical trial subject administered a medicinal product and which does not necessarily have a causal relationship with the treatment. This includes events not seen at baseline or worsened if present at baseline.

The following should not be recorded as AEs if recorded at screening:

Pre-planned procedure unless the condition for which the procedure was planned has worsened since baseline Pre-existing conditions found as a result of screening procedures Changes in common cold symptoms (i.e. worsening of rhinorrhea, nasal congestion, sore throat, cough, and headache).

Severity Assessment

Mild: Transient symptoms, no interference with the subject's daily activities

Moderate: Marked symptoms, moderate interference with the subject's daily activities Severe: Considerable interference with the subject's daily activities, unacceptable Efficacy Analyses The two primary endpoints are rhinorrhea and nasal congestion during the first 24-hour period.

Rhinorrhea recorded as the number of used paper tissues during the trial will be log transformed and analysed using a linear model, including treatment, country and rhinorrhea score at screening as terms in the model. Other secondary efficacy endpoints are the subjective evaluation of nasal congestion (for the remaining trial period), rhinorrhea (for the remaining period) both scored once daily on a 4-point scale, and a composite score of both symptoms. For these variables the AUC (day 1 to 7) will be calculated, log-transformed and analysed using a linear model including treatment, country and the respective score at screening as terms in the model. The score on a 5-point scale of general impression will be analysed using a similar approach as for the two primary endpoints.

The invention claimed is:

1. A composition in the form of an aqueous solution comprising:
   a) ipratropium or a salt thereof in an amount from 0.2 mg to 2 mg per mL,
   b) xylometazoline or a salt thereof in an amount from 0.4 mg to 5 mg per mL,
   c) at least one complex binder selected from the group consisting of edetic acid, pentetic acid, nitrilotriacetic acid, malonic acid, succinic acid, glutaric acid, adipic acid, pimelic acid, tartaric acid, malic acid, cortic acid, and salts thereof,
   d) at least 10% water, and
   e) 85% glycerol in an amount of 27.0 to 27.9 mg per mL, wherein the solution has a pH in the range from 4.5 to 5.5.

2. The composition according to claim 1, wherein the complex binder is edetic acid or a salt thereof.

3. The composition according to claim 1, wherein the ipratropium or a salt thereof is selected from the group consisting of ipratropium bromide, ipratropium chloride, ipratropium iodide, ipratropium fluoride and ipratropium hydroxide.

4. The composition according to claim 1, wherein the xylometazoline or a salt thereof is selected from the group consisting of xylometazoline hydrochloride, xylometazoline hydrobromide, xylometazoline hydroiodide, xylometazoline hydrofluoride, xylometazoline sulphate, xylometazoline nitrate, xylometazoline formate, xylometazoline acetate, xylometazoline citrate, xylometazoline tartrate and xylometazoline fumarate.

5. The composition according to claim 1, wherein a) the ipratropium or a salt thereof is ipratropium bromide in an amount from 0.2 mg to 2 mg per mL; b) the xylometazoline or a salt thereof is xylometazoline hydrochloride in an amount from 0.4 mg to 5 mg per mL; and c) the complex binder is disodium edetate in an amount from 0.1 mg to 10 mg per mL.

6. The composition according to claim 1, which is a nasal composition.

7. The composition according to claim 1, wherein
   a) the ipratropium or a salt thereof is ipratropium bromide in an amount of 0.2 mg per mL;
   b) the xylometazoline or a salt thereof is xylometazoline hydrochloride in an amount of 1 mg per mL;
   e) the 85% glycerol is in an amount of 27.3 mg per mL; and the solution has a pH of 4.5.

8. The composition according to claim 1, wherein
   a) the ipratropium or a salt thereof is ipratropium bromide in an amount of 1.2 mg per mL;
   b) the xylometazoline or a salt thereof is xylometazoline hydrochloride in an amount of 1 mg per mL;
   c) the complex binder is disodium edetate in an amount of 0.5 mg per mL;
   e) the 85% glycerol is in an amount of 2.70% (w/v); and the solution has a pH of 4.5.

9. The composition according to claim 1, wherein
   a) the ipratropium or a salt thereof is ipratropium bromide in an amount of 1.2 mg per mL;
   b) the xylometazoline or a salt thereof is xylometazoline hydrochloride in an amount of 1 mg per mL;
   c) the complex binder is disodium edetate in an amount of 0.5 mg per mL; and
   the solution has a pH of 4.5.

10. The composition according to claim 1, wherein
    a) the ipratropium or a salt thereof is ipratropium bromide in an amount of 0.6 mg per mL;
    b) the xylometazoline or a salt thereof is xylometazoline hydrochloride in an amount of 1.0 mg per mL;
    c) the complex binder is selected from the group consisting of disodium edetate, calcium dinatrium edetate, dipotassium edetate, and trisodium edetate in an amount of 0.125 mg per mL;
    (e) the 85% glycerol is in an amount of 27.3 mg per mL; and
    the solution has a pH of 4.5.

11. The composition according to claim 1, wherein
    (a) the ipratropium or salt thereof is ipratropium bromide in an amount of 0.600 mg,
    (b) the xylometazoline or salt thereof is xylometazoline hydrochloride in an amount of 0.500 mg,
    (c) the complex binder is disodium edetate in an amount of 0.500 mg,
    (d) the water is purified water in an amount to result in a total volume of 1 mL,
    (e) the 85% glycerol is in an amount of 27.9 mg, and wherein the composition further comprises concentrated hydrochloric acid and sodium hydroxide in an amount to adjust the pH to 4.5.

12. A method for the treatment of a condition selected from the group consisting of rhinitis and nasal congestion comprising administering co-instantaneously to a mucosa of a human ipratropium or a salt thereof in a therapeutically effective amount of from 0.2 mg to 2 mg per mL and xylometazoline or a salt thereof in a therapeutically effective amount of from 0.4 mg to 5 mg per mL formulated in an aqueous solution with a pH in the range from 4.5 to 5.5 and at least one complex binder selected from the group consisting of edetic acid, pentetic acid, nitrilotriacetic acid, malonic acid, succinic acid, glutaric acid, adipic acid, pimelic acid, tartaric acid, malic acid, cortic acid, and salts thereof, wherein the solution comprises at least 10% water and 85% glycerol in an amount of 27.0 to 27.9 mg per mL.

13. The method according to claim 12, wherein the administration delivers a dosage unit having a volume of about 10 to 500 µL.

14. The method according to claim 12, wherein the administration delivers the ipratropium or a salt thereof in a unit dose therapeutically equivalent to an amount of about 5 µg to 800 µg of ipratropium bromide; and wherein the administration further delivers the xylometazoline or a salt thereof in a dose therapeutically equivalent to an amount of about 5 µg to 700 µg of xylometazoline hydrochloride.

15. The method according to claim 12, wherein the administration delivers a daily dose of the ipratropium or a salt thereof in a dose therapeutically equivalent to an amount of about 50 µg to 1500 µg of ipratropium bromide; and wherein the administration further delivers a daily dose of the xylometazoline or a salt thereof in a dose therapeutically equivalent to an amount of about 40 µg to 1300 µg of xylometazoline hydrochloride.

16. The method according to claim 12, wherein the administration is to one or both nostril(s) for one to four times daily.

17. A method for the treatment of a condition selected from the group consisting of rhinitis and nasal congestion comprising administering co-instantaneously to a mucosa of a human a therapeutically effective amount of ipratropium or a salt thereof and xylometazoline or a salt thereof formulated in an aqueous solution with a pH in the range from 4.5 to 5.5; wherein the administration delivers a composition as defined in claim 1.

18. A method for the treatment of a condition selected from the group consisting of rhinitis and nasal congestion comprising administering co-instantaneously to a mucosa of a human a therapeutically effective amount of ipratropium or a salt thereof and xylometazoline or a salt thereof formulated in an aqueous solution with a pH in the range from 4.5 to 5.5; wherein the administration delivers a composition as defined in claim 2.

19. A method for the treatment of a condition selected from the group consisting of rhinitis and nasal congestion comprising administering co-instantaneously to a mucosa of a human a therapeutically effective amount of ipratropium or a salt thereof and xylometazoline or a salt thereof formulated in an aqueous solution with a pH in the range from 4.5 to 5.5; wherein the administration delivers a composition as defined in claim 3.

20. A method for the treatment of a condition selected from the group consisting of rhinitis and nasal congestion comprising administering co-instantaneously to a mucosa of a human a therapeutically effective amount of ipratropium or a salt thereof and xylometazoline or a salt thereof formulated in an aqueous solution with a pH in the range from 4.5 to 5.5; wherein the administration delivers a composition as defined in claim 4.

21. A method for the treatment of a condition selected from the group consisting of rhinitis and nasal congestion comprising administering co-instantaneously to a mucosa of a human a therapeutically effective amount of ipratropium or a salt thereof and xylometazoline or a salt thereof formulated in an aqueous solution with a pH in the range from 4.5 to 5.5; wherein the administration delivers a composition as defined in claim 5.

22. A method for the treatment of a condition selected from the group consisting of rhinitis and nasal congestion comprising administering to a mucosa of a human in need thereof a composition in the form of an aqueous solution comprising:
    (a) ipratropium bromide in an amount of 0.2 mg to 2 mg per mL;
    (b) xylometazoline hydrochloride in an amount of 0.4 mg to 5 mg per mL;
    (c) disodium edetate in an amount of 0 to 10 mg;
    (d) purified water in an amount to result in a total volume of 1 mL; and
    (e) 85% glycerol in an amount of 27.0 to 27.9 mg per mL;
    wherein the solution has a pH of 4.5 to 5.5.

23. The method according to claim 22, wherein the aqueous solution comprises:
    (a) ipratropium bromide in an amount of 0.3 to 1.2 mg per mL;
    (b) xylometazoline hydrochloride in an amount of 1 mg per mL;
    (c) disodium edetate in an amount of 0.5 mg;
    (d) purified water in an amount to result in a total volume of 1 mL; and
    (e) 85% glycerol in an amount of 27.0 to 27.5 mg per mL;
    wherein the solution has a pH of 4.5.

\* \* \* \* \*